United States Patent [19]
Grisham et al.

[11] Patent Number: 5,210,417
[45] Date of Patent: May 11, 1993

[54] MODULATED HIGH SENSITIVITY INFRARED POLARIMETER

[75] Inventors: John A. Grisham, Rogersville; Frederick W. Clarke, Madison; Charles R. Christensen, Athens; John L. Stensby, Madison, all of Ala.

[73] Assignee: The United States of America as represented by the Secretary of the Army, Washington, D.C.

[21] Appl. No.: 839,627

[22] Filed: Feb. 24, 1992

[51] Int. Cl.$^5$ ............................................. G01N 21/21
[52] U.S. Cl. .................. 250/338.1; 356/367; 356/370; 356/368
[58] Field of Search ............. 356/367, 370, 368; 250/338.1

[56] References Cited
U.S. PATENT DOCUMENTS 4,637,726  1/1987  Walker et al. ................ 356/367
4,818,881  4/1989  Tanton et al. ................ 250/338.1

OTHER PUBLICATIONS

V. A. Yatsenko and V. A. Bokov, "Magnetooptical Apparatus for Measuring the Faraday Effect and Susceptibility of Magnetic Films." Translated from *Pribory i Tekhnika Eksperimeta*, No. 4 (Jul.–Aug. 1979) pp. 227–230, Copyright Ⓡ 1980 Plenum Publishing Corporation.

"A Nondestructive Testing Technique for Characterizing Infrared Detector/Focal Plane Array Material" by Frederick W. Clarke, Charles R. Christensen, John A. Grisham and John L. Stensby, Jan. 1991.

*Primary Examiner*—Constantine Hannaher
*Attorney, Agent, or Firm*—Freddie M. Bush; Hay Kyung Chang

[57] ABSTRACT

A modulated Faraday rotation signal is produced by passing a linearly polarized laser beam through a semiconductor wafer sample in a modulated magnetic field that is induced in an electromagnet by a sine wave generator and driver coupled thereto. The rotation signal is normalized by dividing by a transmission signal produced by modulating the beam with a chopper that operates at a different frequency from the frequency of the driver. The result is a Faraday rotation measurement with high signal-to-noise ratio and compensation for laser drift in intensity.

2 Claims, 1 Drawing Sheet

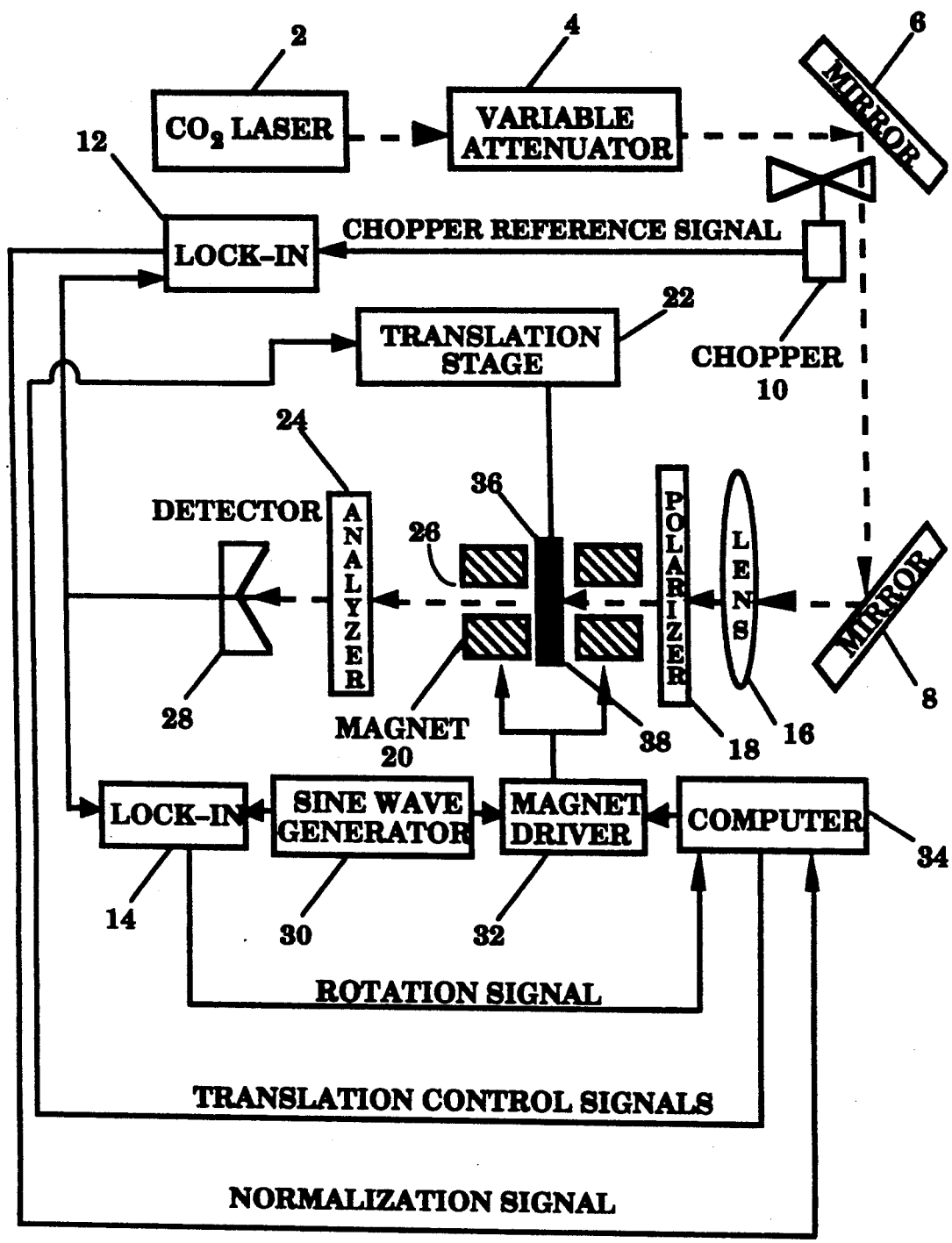

MODULATED HIGH SENSITIVITY INFRARED POLARIMETER

DEDICATORY CLAUSE

The invention described herein may be manufactured, used, and licensed by or for the Government for governmental purposes without the payment to us of any royalties thereon.

BACKGROUND OF THE INVENTION

Detailed characterization of semiconductor materials with respect to a number of parameters is required for screening the material prior to using it in semiconductor production. Such characterization helps to increase yields and reduce costs, as well as provide a general tool to improve materials manufacturing processes. One well-recognized parameter is the free-carrier concentration. The most widely-used technique for determining free-carrier concentration in semiconductor materials is the Hall technique. This technique requires that contacts be soldered to the material and yields an average carrier concentration across the sample material. The Hall technique is time-consuming, requires skilled personnel, is likely to contaminate the sample and is not particularly useful with thin surface films. The current state of the art of measuring Faraday rotation which is linearly dependent on the free-carrier concentration in the sample is set forth in U.S. Pat. No. 4,818,881 by Tanton et al. John A. Grisham is a co-inventor in the Tanton patent which describes a high sensitivity infrared polarimeter that measures Faraday rotation in a small area of a semiconductor wafer sample. The Tanton polarimeter uses a beam chopped at a particular frequency which is detected and a signal extracted via a lock-in amplifier referenced to the chopper frequency. The Faraday rotation is obtained as a signal that is directly proportional to the intensity of the laser beam incident upon the detector at the chopper frequency. This provides high signal-to-noise ratio rotation measurements.

SUMMARY OF THE INVENTION

Modulated High Sensitivity Infrared Polarimeter, herein referred to as Modulated Polarimeter, allows rotation signal to be produced by passing a linearly polarized laser beam through a semiconductor wafer sample in a modulated magnetic field. The rotation signal is normalized by dividing by a transmission signal that is produced by modulating the beam with a chopper which operates at a frequency that is different from the frequency used to modulate the magnetic field. The result is a Faraday rotation measurement with higher signal-to-noise ratio, compensation for variations in sample absorption and compensation for laser drift in intensity. It also provides for nearly simultaneous measurement of Faraday rotation and absorption at each point on the sample.

DESCRIPTION OF THE DRAWINGS

The single figure is a schematic depiction of a preferred embodiment of the invention.

DESCRIPTION OF A PREFERRED EMBODIMENT

Turning now to the Figure wherein like numbers refer to like parts and solid line arrows and dotted line arrows indicate electrical connections and optical paths, respectively, the operation of a preferred embodiment of the invention is herein described.

$CO_2$ laser 2 is set to emit a radiation beam of a desired wavelength. Thence, the beam impinges on attenuator 4 and is attenuated by it to a desired intensity. From attenuator 4, the beam travels to mirror 6 which reflects the beam to mirror 8. Beam chopper 10 set to rotate at a high, given frequency is located in the optical path between mirrors 6 and 8 and interrupts the beam, as it passes, to produce the normalization signal. An electrical signal of the same frequency is output from the chopper and input to first lock-in amplifier 12 which is suitably connected to the chopper. The electrical signal will be used subsequently as a reference by lock-in amplifier 12 in recognizing and extracting the normalization signal from detector 28.

From mirror 8, the beam travels to lens 16 and is focused thereby before continuing to polarizer 18. Polarizer 18 linearly polarizes the beam. Thence, the focused, polarized and chopped beam passes through electromagnet 20 which has aperture 26 running through the center to allow the beam to traverse therethrough. Electromagnet 20 is comprised of two co-axial coils with space 38 between them. Semiconductor wafer sample 36 is placed within space 38 so that the induced magnetic field lines pass through the wafer sample in the same direction as the beam passing through aperture 26. Electromagnet 20 is driven by a sinusoidal current from sine wave generator 30 and driver 32. The driver is set at a high frequency that is different from the chopper frequency used to produce the normalization signal. The sinusoidal current from sine wave generator 30 is input to driver 32 which then amplifies the current and couples it to electromagnet 20 where it produces an alternating magnetic field. As the focused, polarized, and chopped beam passes through the sample, rotation of the plane of polarization of the linearly polarized beam occurs. This is called the Faraday rotation. The magnitude of the free-carrier induced portion of the Faraday rotation is linearly dependent on the free-carrier concentration in the sample at the point of the beam passage. The direction of the rotation changes with the direction of the magnetic field as it is varied due to the sinusoidal current. This change in direction produces an alternating Faraday rotation signal of the driver frequency superimposed on the chopped beam. An electrical signal of the driver frequency is sent from sine wave generator 30 to second lock-in amplifier 14 to be used subsequently as a reference by the second lock-in amplifier in recognizing and extracting the Faraday rotation signal from detector 28. After leaving electromagnetic 20, the beam passes through analyzer 24 which is set at a given desired bias angle depending on the signal analysis method used, before impinging on detector 28. Detector 28 detects the normalizing signal and the rotation signal as signals varying in intensity at their respective frequencies and produces a single electrical signal corresponding to the total intensity of the beam incident on the detector.

Lock-in amplifiers 12 and 14, each being suitably coupled to detector 28 recognize and extract from the detector the normalization and rotation signals, respectively, using the chopper frequency signal and the driver frequency signal as references. The normalization and rotation signals are extracted as rms (root mean square) voltages which are sent from the lock-in amplifiers to input ports of computer 34. Computer 34 uses the rms voltages to calculate the magnitude of the Faraday rotation at the particular point in wafer sample 36 through which the beam passed. After calculating the Faraday rotation, computer 34 manipulates X-Y translation stage 22, which is electrically connected to the computer, to re-position the wafer sample for Faraday rotation measurement at a second point on the sample. When the Faraday rotation is calculated at this second point, the re-positioning step is repeated until measurements have been made at all of the pre-programmed points. Using the series of Faraday rotation measurements thus made and a suitable software package, a contour map of Faraday rotation across the wafer sample can be produced.

For simultaneous normalization and rotation signal operation, analyzer 24 is set to a bias angle that is large with respect to the expected rotation. For non-simultaneous operation, the normalization signal is transmitted separately from the rotation signal by turning off electromagnet 20. The rms value of the normalization signal is extracted and input to computer 34 where it is stored. Then computer 34, which is electrically connected to driver 32, causes the driver to turn on electromagnet 20 and receives therefrom the rms values of the rotation signal and records it. The normalization signal may be transmitted to computer 34 just before or just after the rotation signal is transmitted to computer 34 as long as the time gap between the signal transmission is short in comparison to the time-dependent laser drift.

In the above-described Modulated High Sensitivity Infrared Polarimeter, the intensity of the beam incident on detector 28 can be approximated as:

$$m(\theta_b^2 + \theta_b\sigma + \sigma^2) \quad (1)$$

where m is the on-off chopper function, $\theta_b$ is the analyzer bias angle and $\sigma$ is the sinusoidal Faraday rotation signal. The component of equation (1) signal that is extracted by lock-in amplifier 14 is proportional to:

$$\text{Faraday Rotation} + 2[\tau_o/T]\theta_b \tau_{rms} \quad (2)$$

where T is the period of the mechanical chopper and $\tau_o/T$ is the duty cycle of chopper 10.

The normalization signal extracted by lock-in amplifier 12 is proportional to:

$$\text{Normalization} = (\theta_b^2/\pi)\sqrt{1 - \cos(2\pi\tau_o/T)} . \quad (3)$$

$\sigma_{rms}$ is computed from equations (2) and (3):

$$\sigma_{rms} = \frac{(\theta_b/\pi)\sqrt{1 - \cos(2\pi\tau_o/T)}}{2(\tau_o/T)} \cdot \frac{\text{Faraday Rotation}}{\text{Normalization}} \quad (4)$$

where the unknown proportionality of equations (2) and (3) due to laser drift and other sources of noise is cancelled.

In the event that normalization and rotation signals are transmitted simultaneously to the computer, the normalization signal extracted from the equation (1) signal is proportional to the time average or d.c. component of $\theta_b^2 + \sigma^2$ which can lead to interference with the normalization signal by the Faraday rotation signal. The normalization signal has the form:

$$\text{Normalization} = \frac{(\theta_b^2 + 1/2\sigma^2)}{\pi}\sqrt{1 - \cos(2\pi\tau_o/T)} . \quad (5)$$

Interference can be minimized to give approximately the same result obtained in Equation (4) if $\theta_b$ is set such that $\sigma$ is small compared to $\theta_b$.

Although a particular embodiment and form of this invention has been illustrated, it is apparent that various modifications and embodiments of the invention may be made by those skilled in the art without departing from the scope and spirit of the foregoing disclosure. Accordingly, the scope of the invention should be limited only the claims appended thereto.

We claim:

1. In a high-sensitivity infrared polarimeter system for measuring the amount of Faraday rotation occurring in a polarized beam as the beam passes through a semiconductor wafer sample in the presence of magnetic field; said polarimeter including a chopper revolving at a first frequency to produce a transmission signal; an analyzer, a detector and an electromagnet comprised of two co-axial coils, said coils having a space therebetween, the improvement for measuring the normalization signal and Faraday rotation signal simultaneously, said improvement comprising: a means for modulating the magnetic field at a second frequency concurrently with the revolution of the chopper; a first lock-in amplifier, said first amplifier being coupled between said chopper and said detector for providing a normalization signal; and a second lock-in amplifier, said second amplifier being coupled between said detector and said generator for providing the Faraday rotation signal.

2. A high-sensitivity infrared polarimeter system as set forth in claim 1, wherein said analyzer is set at as bias angle, said angle being large with respect to the expected Faraday rotation.

* * * * *